United States Patent
Pu

(10) Patent No.: US 6,854,470 B1
(45) Date of Patent: Feb. 15, 2005

(54) CIGARETTE SIMULATOR

(76) Inventor: Danming Pu, Garden House, No. 309 Main Street, Jinyuling, Nanchong City, Sichuan 637000 (CN)

( * ) Notice: Subject to any disclaimer, the term of this patent is extended or adjusted under 35 U.S.C. 154(b) by 0 days.

(21) Appl. No.: 09/355,581

(22) PCT Filed: Nov. 27, 1998

(86) PCT No.: PCT/CN98/00279

§ 371 (c)(1),
(2), (4) Date: Feb. 23, 2000

(87) PCT Pub. No.: WO99/27806

PCT Pub. Date: Jun. 10, 1999

(30) Foreign Application Priority Data

Jan. 12, 1997 (CN) .......................... 97107802 A

(51) Int. Cl.[7] .......................... A24F 47/00; A24B 15/16; A24D 1/18
(52) U.S. Cl. .......................... 131/273; 131/275; 131/276; 128/202.21
(58) Field of Search ................. 131/194, 195, 131/196, 198.1, 271, 273, 275, 276; 128/202.21

(56) References Cited

U.S. PATENT DOCUMENTS

| | | | |
|---|---|---|---|
| 5,269,327 A | * | 12/1993 | Counts et al. ......... 128/200.14 |
| 5,591,368 A | * | 1/1997 | Fleischhauer et al. ...... 131/194 |
| 5,613,505 A | | 3/1997 | Campbell et al. |
| 5,666,977 A | * | 9/1997 | Higgins et al. ........ 128/200.14 |
| 5,692,525 A | * | 12/1997 | Counts et al. ............... 131/194 |
| 5,845,649 A | * | 12/1998 | Saito et al. .................. 131/194 |
| 5,865,185 A | * | 2/1999 | Collins et al. ......... 128/200.14 |
| 6,125,853 A | * | 10/2000 | Susa et al. ................... 131/194 |
| 6,155,268 A | * | 12/2000 | Takeuchi ..................... 131/194 |

FOREIGN PATENT DOCUMENTS

| | | |
|---|---|---|
| CN | 87103774 A | 10/1988 |
| CN | 1035762 A | 9/1989 |
| CN | 2045579 U | 10/1989 |
| CN | 2047485 U | 11/1989 |
| CN | 1105217 A | 7/1995 |
| EP | 0520231 A2 | 12/1992 |

* cited by examiner

Primary Examiner—James Derrington
Assistant Examiner—Carlos Lopez
(74) Attorney, Agent, or Firm—Christensen O'Connor Johnson Kindness PLLC

(57) ABSTRACT

A non-smoking, non-ash, and non-combustible cigarette simulator. When the cigarette is smoked, electrical, magnetic, sonic, light and aromatic effects occur.

3 Claims, 1 Drawing Sheet

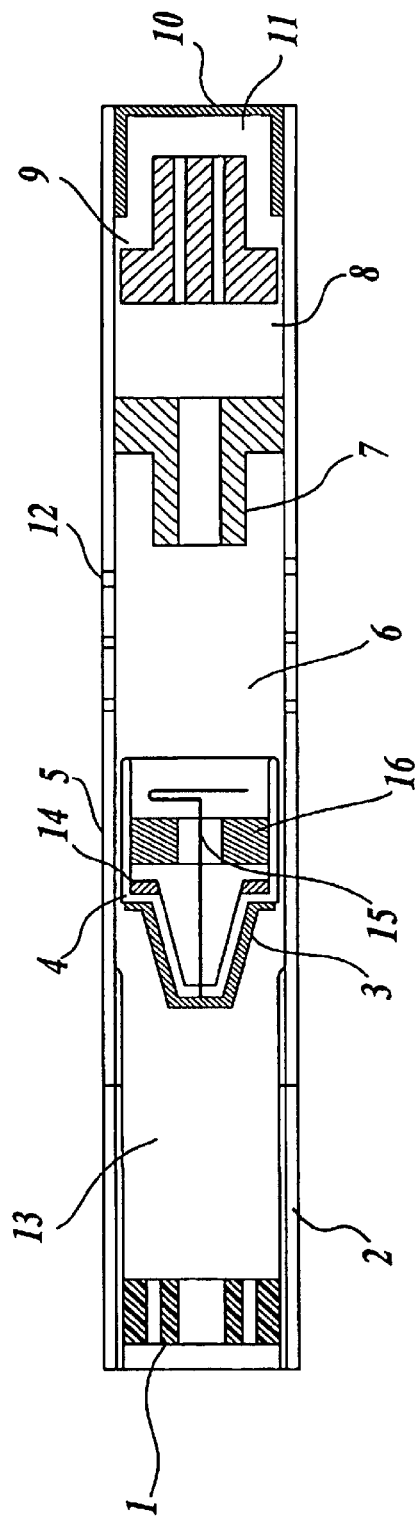
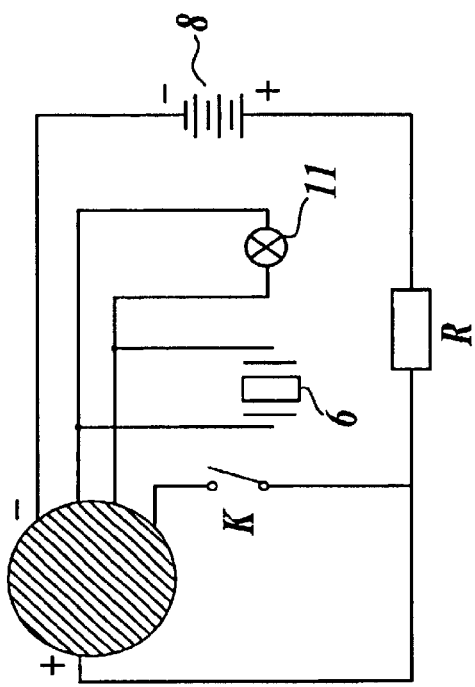
Fig.1.
Fig.2.

CIGARETTE SIMULATOR

FIELD OF THE INVENTION

This invention relates to a kind of cigarettes, particularly, a cigarette-like article which does not burn, but sparkles and/or plays a music piece.

BACKGROUND OF THE INVENTION

Usually, people while smoking burn up one end of a cigarette giving rise to mist or smoky fog that passes through one's mouth, tongue, throat, nose and other sense organs, and then reaches one's lung to stimulate said organs and nerves satisfying the smoker's physiological, psychological or social needs for his enjoying the fun of smoking. This way of smoking has many shortcomings. Such harmful components as nicotine, cigarette tar, CO, benzopyrene, acetone, arsenic and DDT contained in the smoke badly damage smokers' health and the carelessness in smoking easily causes fire, or loss of properties. These turn out to be the main reasons for prohibiting or quitting smoking. Tobacco smoke is rated by WHO as one of the A class cancer-causing components and a worldwide tendency of dropping cigarette smoking prevails. On one hand, all the countries on earth are taking measures for introducing limitations on tobacco production; but, on the other hand, millions of smokers are raising even more demands for tobacco, thus making smoking one of the largest troubles of the world.

CN1045691A provides a smoking article making use of an electrical resistance heating element and an electric power source that bring forth tobacco flavor or haze and lead to smoking-like effect.

CN 2047887U discloses a smoking device with solid extract containing some extracts and Chinese traditional medicine.

CN 2226826Y discloses a unharmful imitation cigarettes comprising a filter and tobacco flavor medium, characterized in that some cigarette filaments and Chinese traditional medicines are installed therein.

CN 1035762A discloses a substitute for cigarettes, the raw materials of which are Chinese traditional medicines.

CN 1107015A discloses a human life-promoting healthy product in which finely cut tobacco is replaced by a natural, good-for-health wild plant after being collected, dried, steamed up, cut into small pieces, baked, and rolled up.

CN 1134800A discloses a non-toxic cigarettes which take tea leaves and chrysanthemum non-toxic to human body as the main raw material instead of nicotine-containing tobacco.

U.S. Pat. No. 5,666,978 discloses a smoking system in which a medium having tobacco flavor is heated by an electric heating element.

In these patent references, some of them are still using tobacco as the raw material wherein the tobacco still burns, thus leading to smoking dusts and stumps pollution or fire accidents due to careless cigarette ignition etc., there can not be found fundamental improvement; some of them are soaking the cut tobacco in the innovated Chinese medicines or using directly the latter to replace tobacco wherein both the smoking feeling and quitting or curing effect are yet not satisfying. These cigarettes can but satisfy smoker's taste or smell preference; with improvement of living conditions, people hope that while smoking, beautiful music can be heard, and vicissitude of lights can be seen, leading to visual and audio enjoyments.

SUMMARY OF THE INVENTION

The present inventor, after an extensive and intensive study, has unexpectedly found and developed a cigarette simulator without ignition and without smoke and stumps pollution, thus eliminating the disadvantages of the prior art. In addition, this cigarette simulator has refreshing taste; while smoking, one can enjoy the fun of audio-, visual-, smell-, and/or magnetic effects simultaneously. And the medical effect of giving up or using substitutes for common cigarettes as well as health care can be obtained by enjoying the fun of cigarette simulators. The present invention is just based on this finding.

PREFERRED EMBODIMENTS OF THE INVENTION

One aspect of the present invention is to provide a cigarette simulator comprising a cigarette tip (2), a cigarette cylindrical body (5), fillings and a control valve; said cigarette tip (2) has one of its end filled with a filtering material constituting the filter (1), and its another end is connected with one end of the cylindrical body (5) in the middle of which are ventholes (12); the cavity between the cigarette tip (2) and the cigarette cylindrical body (5) is a flavor medium cylinder (13) filled with the fillings and the control valve is inside the cigarette cylindrical body (5) close to the end of the cigarette tip, said control valve is contacted with the inner cylindrical body (4), the end close to the cigarette tip of the inner cylindrical body (4) is in the form of an opening like an upset trumpet and over which there is an upper cover (3) accordant with its form, at the bottom of the upper cover and at the root of the trumpet of the inner cylindrical body (4) are magnetic rings (14), the two magnetic rings have opposite magnetic poles; at the inner side of the other end of the cylindrical body (5) is a splint (7) in the form of a fork and said end is connected with the cap cover (10). This cigarette makes neither sound, nor light.

Another aspect of the present invention is a cigarette simulator comprising a cigarette tip (2), a cigarette cylindrical body (5), fillings, a control valve, and a light-emitting mechanism; said cigarette tip (2) has one of its ends filled with filtering material constituting the filter (1), and its another end is connected with one end of the cylindrical body (5) in the middle of which are ventholes (12), the cavity between the cigarette tip (2) and the cylindrical body (5) is the flavor medium cylinder (13) filled with the fillings, inside the cylindrical body (5) is the control valve at the one end close to the cigarette tip, the control valve is connected with the inner cylindrical body (4), inside the inner cylindrical body there is an electrically conducting front inner plate (16) having a hollow hole, the end of the inner cylindrical body (4) close to the end of the cigarette tip is in the form of opening like an upset trumpet over which there is an upper cover (3) accordant with its form, the magnetic rings (14) are set at the bottom of the upper cover and at the root of the trumpet of the inner cylindrical body (4), the two magnetic rings have opposite magnetic poles, the middle portion of the upper cover (3) is fixed with one end of the "T" or the "τ" shape conducting wire (15) going through the central hole of the inner plate (16), the other end of the cylindrical body (5) has at its inner side a fork-shape splint (7), a power source (8) and a lamp socket (9), on the splint (7) there is an integrated circuit module controlling the light-emitting mechanism, the power source (8) is a button battery connected with a conducting wire, the lamp socket (9) is cylindrical, in the middle of which are two small holes used as the fixed holes of the two poles of the light-emitting part (11), the end portion of the cylindrical body (5) is connected with the cap cover (10). This cigarette only emits light because the positive and negative magnetic poles of the control valve are reversibly connected.

Still another aspect of the present invention is a cigarette simulator comprising a cigarette tip (2), a cylindrical body (5), fillings, a control valve, and an audio-visual mechanism, said cigarette tip (2) has its one end filled with a filtering material constituting the filter (1), and its another end is connected with one end of the cylindrical body (5) in the middle of which are ventholes (12), the cavity between the cigarette tip (2) and the cylindrical body (5) is the flavor medium cylinder (13) filled with the fillings, the cylindrical body (5) has in it the control valve at its end close to the cigarette tip, the control valve is connected with the inner cylindrical body (4), inside the inner cylindrical body is an electrically conducting front inner plate (16) having a hollow hole, the inner cylindrical body (4) is in a form of an opening like an upset trumpet at its end close to the cigarette tip, over which there is an upper cover (3) accordant with the form, the magnetic rings (14) are set at the bottom of the upper cover and at the root of the trumpet of the inner cylindrical body (4), the two magnetic rings have opposite magnetic poles, the middle portion of the upper cover (3) is fixed with one end of the "T" shape or "τ" shape conducting wire (15) going through the central hole of the inner plate (16), the other end of the cylindrical body (5) has at its inner side the fork-shape splint (7), a power source (8), and a lamp socket (9); on the splint (7) is fixed an integrated circuit module and a humming sheet (6) controlling the audio-visual mechanism, on the outer wall of the cylindrical body (5) positioned with the humming sheet (6) are ventholes (12), power source (8) is a button battery connected with a conducting wire, the lamp socket (9) is cylindrical, in the middle of which are two small holes used as fixing holes for the two poles of the light-emitting part (11), the ending portion of the cylindrical body (5) is connected with the cap cover (10). The positive and negative magnetic poles of the control valve for this cigarette simulator are connected positively in order to make sound and emit light.

For the cigarette simulators as indicated in the above items 1–3, the fillings in the flavor medium cylinder comprise a volatile cigarette perfume extract and one of prescription A, B, C, D or E by weight parts:

A. dichroa leaf 15–20, sesame leaf 25–35, licorice 6–10, borneol 10–15, mugwort leaf 18–23 and mint 15–20;

B. asarum 10–15, mint 10–15, perilla leaf 15–18, nardostachys 10–15, cinnamon 6–10, angelica 25–35, borneol 10–15, and chrysanthemum 18–23;

C. tussilago 15–20, cynanchum 10–15, acorus 5–20, perilla leaf 25–35 and sesame leaf 25–35;

D. borneol 10–15, sandalwood 25–35, acorus 15–20, asarum 12–18 and licorice 6–10;

E. ganoderma 15–20, cinnamon 10–15, asarum 12–18, bearded scutellaria 19–23, oldenlandia 25–35 and pepper 10–15;

wherein ratio of the weight parts for the various components of the volatile cigarette perfume extract read as follows:
osmanthus leaf oil 19–23, flavor lemonade oil 15–20, isobutyl salicylate 10–15, phenylethanol 10–15 and anisaldehyde 10–15.

For the cigarette simulator as indicated in the above items 1–3, the cap cover (10) stated thereabove is the cap cover of higher transparency prepared by a transparent material, preferably polyethene.

As it can be seen from the above-indicated, the object of the present invention may be realized. The invention not only can be used for storing the medicine flavor, but also be turned out to be very good article for inhaling the medicine flavor; it looks like a cigarette, accompanying with particular electrical-, magnetic-, audio-, video- and/or perfuming-effects. While simulating smoking, a negative pressure is produced in the cigarette body, the peripheral air enters the cigarette body through the air hole and then through the inner cylinder, pushing open (i.e., triggering) the upper cover, and the air passes simultaneously the medicine-cigarette casing, turning out to be the carrier of the medicine flavor to be inhaled into the mouth cavity joining the blood circulation, then a red light sparkles and a beautiful musical piece starts to play automatically, bringing the smoker unlimited fun and happiness. The medicine gas of unique cigarette perfume can not only bring forth refreshment and revitalization, but also drop away a craving for tobacco in a certain period of time, assuming significant effect of dropping smoking cigarette or substituting for cigarette smoking. The unique outstanding feature of said product is having kept the smoker common habitual style; once a mouthful of Chinese medicine flavor is inhaled instead of harmful tobacco flue, sparking red light can be found instead of dangerous burning and an amusing musical piece is simultaneously performed, such harmony of sound, light, magnetism, and flavor being pleasing to the smoker.

One thing should be mentioned here: prescriptions A, B, C, and D are prescriptions for giving up smoking or substituting smoking.

BRIEF DESCRIPTIONS OF THE ATTACHED DRAWINGS

FIG. 1 is a structural scheme of the cigarette simulator.

FIG. 2 shows the electrical circuit principle of the cigarette simulator.

The invention will be further described in combination with the attached drawings and examples. It should be understood that these examples are intended to explain the present invention without limiting the present invention.

EXAMPLES

Example 1

According to the following weight parts, the Chinese traditional medicines are taken as a prescription for giving up smoking or substituting smoking: dichroa leaf 15, sesame leaf 30, licorice 10, borneol 15, mugwort leaf 21 and mint 15. After having been processed, these Chinese traditional medicines are ground into solid powder agent, and then mixed up homogeneously for use.

The cigarette perfume extract is prepared according to the following weight parts: osmanthus leaf oil 19, flavor lemonade oil 18, isobutyl salicylate 15, phenylethanol 10 and anisaldehyde 12; these components are then mixed up homogeneously for use. And then, the traditional medicines after being processed are ground into solid powder as the fillings after being fed with the cigarette perfume extract.

A cigarette simulator is provided, which comprises a cigarette tip, a cigarette cylindrical body, fillings, and also a control valve and a audio-visual mechanism. On end of the cigarette tip (2) is filled with the filtering material to constitute the filter (1), while the other end is connected with one end of the cigarette cylindrical body (5) in the middle of which are the ventholes. The cavity between the cigarette tip (2) and the cylindrical body (5) is the flavor medium cylinder (13) filled with the filling. The cylindrical body (5) has in it a control valve close to the cigarette tip end, the control valve is contacted with a inner cylindrical body. The inner cylindrical body 4 has in it an electrically conducting front inner plate (16) having a hollow hole. The inner cylindrical body (4) is in the form of an opening like an upset trumpet close to the cigarette tip end, over which is an upper cover (3) accordant with its form. Magnetic rings (14) are set at root of the upper cover and at the root of the trumpet of the inner cylindrical body (4), the two magnetic rings have opposite magnetic poles, the middle portion of the upper cover (3) is fixed with one end of the "T" shape or "τ" shape conducting wire (15) going through the central hole of the inner plate (16), the other end of the cylindrical body (5) has in its inner side a fork-shape splint (7), a power source (8), and a lamp socket (9), on the outer wall of the cylindrical body (5) positioned with the humming sheet (6) are set up air holes (12), on the splint (7) are fixed the integrated circuit module and humming sheet for controlling audio-visual mechanism. The power source is a button battery connected with the electrical parts respectively by means of the conducting wire, and its circuitry block diagram is as shown in FIG. 2. The humming sheet (6) and the integrated circuit are the core portion of the entire audio-visual mechanism. The humming sheet (6) and the light-emitting part (11) are respectively connected with the two output legs of the integrated circuit module, and said integrated circuit module has on it further connected power source (8) and switch K, i.e., the gate of the control valve, the electrical circuit has further a resistance R connected in series to increase the resistance value and to lengthen the use time. The lamp socket (9) is cylindrical, in the middle of which are two small holes used as the fixing holes of the two poles of the light-emitting part (11). The ending portion of the cylindrical body (5) is connected with the cap cover (10).

The flavor medium casing accommodating the Chinese traditional medicines and the volatile cigarette perfume extract is positioned between the upper cover (3) and the filter. While being assembled, the ready-made fillings are put into the cavity of the cigarette tip, then the other end of the cigarette tip is connected with one end of the cylindrical body having in its middle the ventholes.

While simulating smoking, a negative pressure is produced in the cylindrical body, the peripheral air enters the cylindrical body through the air holes and pushes open (i. e., triggering) the upper cover through the inner cylinder, then the air passes again the medicine flavor casing, turning out to be the carrier of the medicine flavor to be inhaled into the mouth to join the blood circulation, and simultaneously a red light sparkles and beautiful amusing musical piece is performed wonderfully, bringing one to unlimited fun and joy.

Example 2

According to the following weight parts, the Chinese traditional medicines are taken as a prescription for pleasing a user: asarum 10, mint 12, perilla leaf 18, nardostachys 15, cinnamon 9, angelica 25, bomeol 15 and chrysanthemum 21.

The cigarette cylindrical body structure and the work principle are the same as these of examples 1.

The cigarette perfume extract is prepared as the following weight parts: osmanthus leaf oil 21, flavor lemonade oil 15, isobutyl salicylate 12, phenylethanol 15 and anisaldehyde 10; these components are then mixed up homogeneously for use. And then, the traditional medicines after being processed are ground into solid powder, put into the flavor medium casing and then are fed with the volatile cigarette perfume extract.

Example 3

According to the following weight parts, the Chinese traditional medicines are taken as a prescription for curing the cough or inflammation: tussilago 15, cynanchum 12, acorus 20, Perilla leaf 25 and sesame leaf 35; the cigarette cylindrical body structure and the work principle are the same as these of examples 1.

Example 4

According to the following weight parts, the Chinese traditional medicines are taken as a prescription for pleasing a user: borneol 10, sandalwood 30, acorns 20, asarum 15 and licorice 10. The cigarette cylindrical body structure and the work principle are the same as those of Example 1.

The cigarette perfume extract is prepared as the following weight parts: osmanthus leaf oil 19, flavor lemonade oil 20, isobutyl salicylate 12, phenylethanol 13 and anisaldehyde 14; these components are then mixed up homogeneously for use. Said Chinese traditional medicines after being processed are ground into solid powder, put into the flavor medium casing, and then the volatile cigarette perfume extract is further injected thereinto.

Example 5

According to the following weight parts, the Chinese traditional medicines are taken as a prescription for pleasing a user: ganoderma 18, cinnamon 15, asarum 12, bearded scutellaria 21, oldenlandia 26 and pepper 14.

The cigarette cylindrical body structure and the work principle are the same as those of example 1.

The cigarette perfume extract is prepared according to the following weight parts: osmanthus leaf oil 20, flavor lemonade oil 18, isobutyl salicylate 14, phenylethanol 12 and anisaldehyde 13; these components are then mixed up homogeneously for use. Said Chinese traditional medicines after being processed are ground into solid powder agent, put into the flavor medium casing, and then the volatile cigarette perfume extract is further injected thereinto.

Applicability Example

The present inventor made an evaluation on the smoking quitting effect of said smoking quitting article in July–September, 1997 in Beijing aiming at 71 smokers of different professions.

I. Clients Under Test And Method (I) Clients Under Test:

smoking-quitting volunteers from institutions, research institutes and army of the present municipality.

(II) Test Method:

1. Test Form

Test forms are used to inquire the followings of the smokers: the age starting to smoke; smoking quantity; smoking years; smoking-quitting history; smoking personnel in the smoker's family; species of home kitchen fuels etc.

2. Method for Smoking Quitting

While the volunteer is smoking orally the smoking-quitting article, the sparkling red light appears instead of harmful cigarette flue or haze, its unique outstanding Chinese traditional medicine flavor will take the place of harmful tobacco flue or haze and simultaneously an amusing musical piece will be performed so as to conquer the quitting interruption of the smoker. In general, each smoker takes two pieces, the effective duration of each piece lasts 20 days, the smoking-quitting therapeutical course lasts 40 days. Herein the smokers are only allowed to smoke the smoking-quitting articles instead of other cigarettes.

3. Health Indices and the Detection Methods Thereof

We make use of the following three health indices to lead the evaluation on the quitting effect: nicotine metabolite in the urine; carbon monoxide (CO) in the exhaled gas, and sulfocyanate in the spit fluid. The half-life of nicotine metabolite in one's body is 20 hours (in the range of 10–37 hour), it is an specific index for detecting the exposure of cigarette haze as determined by the barbituric acid test. The half-life of carbon monoxide in one's body is less than 1 hour, and while at rest it is 3–4 hours. Said CO in the exhaled air is determined by the electrical potential method. The half-life of sulfocyanate in one's body is very long, about 7–14 days; the content of sulfocyanate in one's spit fluid is determined by the test paper method.

4. Indices of Evaluation on Smoking Quitting Effect

We make use of three health indices of the non-smoker as a criterion for the indices of evaluation on the smoking quitting effect. As is reported by foreign literature, the contents of nicotine metabolites in the morning and the afternoon urine of the non-smokers (average and criterion difference) are respectively $0.7 \pm 0.2$ $\mu$g/mg creatinine and $0.9 \pm 0.2$ $\mu$g/mg creatinine; the concentrations of carbon monoxide in the exhaled air and of sulfocyanate in the spit fluid of the non-smokers are respectively 6 ppm and <30 $\mu$g/ml. The evaluated criteria of the quitters reads as follows:

(1) Total effectiveness: quitting rate+significant effective rate+effective rate;
(2) quitting rate: percentage of the cigarette-quitted persons among the total number of persons under test;
(3) significant effective rate: percentage of the smokers having their smoking quantity dropped above 50% among the total number of persons under test;
(4) effective rate: percentage of the smokers having their smoking quantity dropping 20–50% among the total number of persons under test;
(5) non-effective rate: percentage of the smokers having their smoking quantity dropping below 20% among the total number of persons under test.

II. Results (I) General

Persons under test this time include 71 smokers of cadre, servicemen, inhabitant, scientific researcher etc. (another 9 persons are not listed in this statistics because they have not been carried out the health indices determination after smoking quitting due to many objective reasons such as going on errand, having no time etc.). The ages of the 71 persons under test ranges 19–71 years old; their average age is 38; the average age then starting to smoke is 20; the youngest starting to smoke is 12; their average smoking quantity is 13 pieces; there are 23 persons smoking above 20 pieces each day; number of smoking years reads 17 years in average. From the above result, it can be seen that the smokers under test are mainly adults and young people having a moderate smoking quantity.

(II) Determination Result of Health Indices

1. Content of Nicotine Metabolite in the Urine

The content of nicotine metabolite in the urine of the smokers can sensitively show the smoking extent of the smokers. Among the 30 smokers (5 of them only had been carried out the determination after smoking-quitting) who have used the quitting article, the nicotine metabolite in the urine of 14 smokers has dropped down to the level of the non-smokers ($0.97 \pm 0.24$ $\mu$g/mg nicotine metabolite, creatinine), the content of the nicotine metabolize in the urine of the other 16 smokers shows no change in comparison with that before smoking quitting. (see Table 1).

TABLE 1

Contents of Nicotine Metabolite, Mg/mg in the urine before and after smoking-quitting

| Group Division | sample quantity | before smoking-quitting average value | difference | after smoking-quitting average value | difference |
|---|---|---|---|---|---|
| Group A | 14 | 1.02 | 0.86 | 0.97 | 0.25 |
| Group B | 16 | 4.19 | 2.91 | 4.42 | 2.54 |

Group A: persons quitted smoking
Group B: smokers having decreased quantity of their smoking.

2. CO Concentration in the Exhaled Air

For 14 smokers after smoking-quitting, the average value of CO in the exhaled air drops from the original 10.10 ppm to 6.36 ppm while for 57 smokers after having used the quitting article, their smoking quantity drops in different degrees and their average value of CO concentration in the exhaled air drops from the original 23.42 ppm to 16.33 ppm (see Table 2).

TABLE 2

CO concentration (ppm) in the exhaled air before and after smoking quitting

| Group Division | sample quantity | before smoking-quitting average value | difference | after smoking-quitting average value | difference |
|---|---|---|---|---|---|
| Group A | 14 | 10.10 | 3.59 | 6.36 | 1.44 |
| Group B | 57 | 23.42 | 12.18 | 16.33 | 9.49 |

3. Concentration of Sulfocyanate in the Spit Fluid

For 14 smokers after having used the smoking-quitting article, the average value of the sulfocyanate concentration in the spit fluid drops from the original 26 $\mu$g/ml to 20 $\mu$g/ml while for 57 smokers after having used the smoking quitting article, their smoking quantity drops in different degrees and the average value of sulfocynate concentration in the spit fluid drops from the original 54.12 $\mu$g/ml to 35.96 $\mu$g/ml (see Table 3).

TABLE 3 concentration of sulfocyanate (Mg/ml) in the spit fluid before and after smoking quitting

| Group Division | sample quantity | before smoking-quitting average value | difference | after smoking-quitting average value | difference |
|---|---|---|---|---|---|
| Group A | 14 | 26.67 | 8.89 | 20.00 | 6.55 |
| Group B | 57 | 54.12 | 30.02 | 35.96 | 17.76 |

(III) Evaluation on Smoking Quitting Effect

Among 71 smokers, the three health indices of 14 smokers after having used the quitting article have dropped to those levels of the non-smokers. The smoking quantity of 57 smokers drops in different degrees, 13 of them have their-smoking quantity dropped to above 50%; 32 of them have their smoking quantity dropped to 20–50% and 12 of them dropped to below 20%. From the above result, it can be found that the total effective rate of the 71 smokers after having used the smoking quitting article reads 83.1% among which the smoking quitting rate reads 19.72%, the significant effective rate reads 18.31% and the effective rate reads 45.07%.

changes of three Health Indices Before and After Cigarette Quitting

| code number | age | age starting to smoke | smoking quantity (pieces each day) | | | smoking duration (years) | nicotine metabolite μg/mg creatinine | | CO (ppm) | | sulfocyanate (μg/ml) | |
|---|---|---|---|---|---|---|---|---|---|---|---|---|
| | | | before cigarette quitting | after cigarette quitting | dropping down rate (%) | | before cigarette quitting | after cigarette quitting | before cigarette quitting | after cigarette quitting | before cigarette quitting | after cigarette quitting |
| 1 | 44 | 20 | 5 | 3 | 40 | 24 | 1.35 | | 12 | 10 | 30 | 20 |
| 2 | 50 | 38 | 20 | 4 | 80 | 12 | 2.35 | 4.46 | 18 | 15 | 30 | 20 |
| 3 | 50 | 24 | 30 | 14 | 53.3 | 26 | 11.92 | | 50 | 37 | 100 | 50 |
| 4 | 41 | 20 | 5 | 5 | 0 | 21 | 2.62 | | 45 | 32 | 50 | 50 |
| 5 | 38 | 20 | 10 | 4 | 60 | 18 | 4.5 | | 35 | 16 | 100 | 50 |
| 6 | 46 | 20 | 20 | 10 | 50 | 26 | 6.04 | | 42 | 17 | 100 | 50 |
| 7 | 47 | 18 | 20 | 16 | 20 | 29 | 2.50 | | 17 | 14 | 100 | 50 |
| 8 | 53 | 33 | 5 | 1 | 80 | 20 | 0.67 | 9.0 | 10 | 5 | 20 | 10 |
| 9 | 39 | 20 | 10 | 0 | 100 | 19 | 0.82 | 1.0 | 7 | 7 | 30 | 30 |
| 10 | 47 | 20 | 10 | 6 | 40 | 27 | 3.5 | 6.99 | 28 | 14 | 50 | 30 |
| 11 | 43 | 16 | 20 | 5 | 75 | 27 | 2.96 | | 28 | 18 | 100 | 50 |
| 13 | 58 | 40 | 10 | 0 | 100 | 18 | 0.85 | 1.11 | 7 | 4 | 20 | 10 |
| 14 | 38 | 20 | 10 | 0 | 100 | 18 | 0.57 | 0.7 | 9 | 7 | 20 | 20 |
| 15 | 59 | 20 | 20 | 16 | 20 | 39 | 4.53 | | 23 | 19 | 50 | 50 |
| 16 | 46 | 20 | 10 | 3 | 70 | 26 | 1.7 | | 10 | 8 | 50 | 50 |
| 17 | 33 | 20 | 20 | 14 | 30 | 13 | 1.77 | | 22 | 11 | 100 | 50 |
| 18 | 56 | 25 | 10 | 5 | 50 | 31 | 5.03 | 10.39 | 25 | 16 | 50 | >30 |
| 19 | 29 | 19 | 5 | 1 | 80 | 10 | 1.18 | 1.65 | 12 | 7 | 20 | 10 |
| 20 | 30 | 18 | 15 | 15 | 0 | 12 | 6.26 | | 37 | 22 | 100 | 50 |
| 21 | 36 | 25 | 20 | 20 | 0 | 11 | 4.12 | | 35 | 23 | 100 | 50 |
| 23 | 39 | 20 | 20 | 0 | 100 | 19 | 0.65 | 0.92 | 7 | 6 | 30 | 20 |
| 24 | 45 | 17 | 10 | 6 | 40 | 28 | 3.09 | | 18 | 8 | 50 | 50 |
| 25 | 38 | 28 | 10 | 0 | 100 | 10 | 3.89 | 0.94 | 15 | 6 | 50 | 30 |
| 26 | 71 | 20 | 10 | 0 | 100 | 51 | 0.86 | 1.34 | 8 | 4 | <30 | 20 |
| 27 | 54 | 20 | 20 | 15 | 25 | 34 | 5.76 | | 17 | 10 | 50 | 50 |
| 29 | 40 | 18 | 10 | 0 | 100 | 32 | 0.51 | 1.32 | 14 | 6 | <30 | 20 |
| 31 | 43 | 18 | 10 | 5 | 50 | 25 | 8.92 | 4.46 | 33 | 8 | 50 | 20 |
| 32 | 33 | 24 | 10 | 2 | 80 | 9 | 5.19 | 5.93 | 26 | 8 | 30 | 20 |
| 33 | 45 | 20 | 10 | 4 | 60 | 25 | 4.41 | 2.47 | 18 | 8 | 50 | 20 |
| 34 | 41 | 20 | 10 | 5 | 50 | 21 | 6.95 | | 50 | 12 | 30 | 20 |
| 35 | 44 | 18 | 20 | 20 | 0 | 26 | 8.57 | | 22 | 18 | 100 | 50 |
| 36 | 40 | 17 | 10 | 0 | 100 | 23 | 0.6 | 1.24 | 10 | 4 | 25 | 20 |
| 37 | 46 | 16 | 15 | 14 | 6.6 | 30 | 6.09 | | 27 | 12 | 100 | 50 |
| 38 | 56 | 18 | 10 | 10 | 0 | 32 | 3.32 | | 20 | 18 | 50 | 50 |
| 39 | 41 | 18 | 20 | 10 | 50 | 23 | 5.23 | 3.8 | 28 | 11 | >30 | 30 |
| 40 | 40 | 20 | 20 | 20 | 0 | 20 | 6.81 | | 38 | 20 | 100 | 100 |
| 41 | 57 | 17 | 10 | 8 | 20 | 30 | 6.76 | | 18 | 15 | 30 | 30 |
| 42 | 54 | 25 | 20 | 10 | 50 | 29 | 24.37 | | 50 | 42 | 75 | 40 |
| 43 | 34 | 10 | 15 | 0 | 100 | 24 | 1.12 | 0.69 | 7 | 7 | 20 | 10 |
| 44 | 49 | 20 | 10 | 7 | 30 | 29 | 5.02 | | 13 | 10 | >30 | <30 |
| 45 | 47 | 20 | 30 | 0 | 100 | 27 | 0.47 | 1.22 | 16 | 7 | 30 | 20 |
| 46 | 31 | 19 | 25 | 5 | 20 | 12 | 10.25 | | 43 | 13 | 50 | >30 |
| 47 | 52 | 30 | 3 | 0 | 100 | 22 | 0.55 | 0.56 | 9 | 7 | 10 | 10 |
| 48 | 49 | 25 | 10 | 8 | 20 | 27 | 5.0 | | 15 | 16 | 50 | 30 |
| 49 | 35 | 20 | 20 | 20 | 0 | 15 | 11.2 | | 36 | 30 | 60 | 50 |
| 50 | 41 | 12 | 15 | 9 | 40 | 29 | 7.59 | | 20 | 15 | 50 | 50 |
| 51 | 33 | 22 | 2 | 1 | 50 | 11 | 0.98 | 3.23 | 13 | 7 | 30 | 20 |
| 52 | 35 | 25 | 5 | 3 | 40 | 10 | 10.3 | 2.48 | 23 | 14 | >30 | 20 |
| 54 | 35 | 25 | 5 | 0 | 100 | 10 | 1.3 | 0.8 | 17 | 7 | 20 | 20 |
| 55 | 30 | 20 | 5 | 1 | 80 | 10 | 2.47 | 2.29 | 6 | 6 | 10 | 10 |
| 56 | 33 | 23 | 5 | 5 | 0 | 10 | | | 21 | 9 | 50 | 30 |
| 57 | 47 | 21 | 20 | 10 | 50 | 26 | 5.16 | | 29 | 16 | 50 | 30 |
| 59 | 58 | 53 | 2 | 0 | 100 | 5 | 1.06 | 0.74 | 8 | 9 | 30 | 30 |
| 60 | 41 | 22 | 10 | 8 | 20 | 19 | | | 22 | 16 | 50 | 30 |
| 61 | 32 | 18 | 15 | 10 | 33.3 | 14 | | 2.97 | 13 | 7 | 30 | <30 |
| 62 | 19 | 14 | 10 | 10 | 60 | 5 | | | 6 | 5.5 | >30 | >30 |
| 63 | 20 | 17 | 10 | 10 | 50 | 6 | | 2.97 | 13 | 14 | >30 | <30 |
| 64 | 25 | 18 | 9 | 9 | 22.2 | 8 | | 4.76 | 10 | 12 | 100 | <30 |
| 65 | 26 | 23 | 3 | 3 | 100 | 3 | | 1.93 | 7 | 8 | 20 | 30 |
| 69 | 20 | 12 | 10 | 10 | 0 | 8 | | 3.92 | 14 | 11 | >30 | >30 |
| 70 | 28 | 20 | 10 | 3 | 70 | 8 | | 1.06 | 6 | 20 | 20 | 20 |
| 71 | 22 | 19 | 3 | 3 | 0 | 3 | | | 10 | 13 | 20 | 20 |
| 72 | 20 | 15 | 15 | 8 | 46.6 | 5 | | | 25 | 53 | 100 | 100 |
| 73 | 22 | 16 | 20 | 15 | 25 | 6 | | | 35 | 37 | 100 | >50 |
| 74 | 20 | 15 | 10 | 5 | 50 | 5 | | | 5 | 10 | 20 | 20 |

-continued changes of three Health Indices Before and After Cigarette Quitting

| code number | age | age starting to smoke | smoking quantity (pieces each day) | | | smoking duration (years) | nicotine metabolite μg/mg creatinine | | CO (ppm) | | sulfocyanate (μg/ml) | |
|---|---|---|---|---|---|---|---|---|---|---|---|---|
| | | | before cigarette quitting | after cigarette quitting | dropping down rate (%) | | before cigarette quitting | after cigarette quitting | before cigarette quitting | after cigarette quitting | before cigarette quitting | after cigarette quitting |
| 75 | 22 | 18 | 8 | 5 | 37.5 | 4 | | | 20 | 22 | 50 | >30 |
| 76 | 26 | 21 | 20 | 15 | 25 | 5 | | | 20 | 14 | >30 | 20 |
| 77 | 23 | 14 | 15 | 10 | 33.3 | 9 | | | 13 | 25 | >30 | >30 |
| 78 | 19 | 12 | 17 | 15 | 11.7 | 7 | | | 50 | 32 | 100 | >30 |
| 79 | 19 | 15 | 6 | 3 | 50 | 44 | | | 25 | 14 | >30 | 20 |
| 80 | 26 | 24 | 10 | 4 | 60 | 2 | | | 15 | 15 | 20 | >30 |

Industrial Applicability

From the above stated, it can be found that the present invention possesses the following merits: the cigarette cylindrical body structure is changed from the igniting type to the non-igniting type; there is no tobacco haze or cigarette end pollution; it has music and red light; the inhaled harmful smoky flue is changed into pleasing medicine flavor; finely extracted medicine flavor takes the place of harmful smoky haze, eliminating the damage of smoking to human body and environment; it is beneficial, convenient, safe and economical.

What is claimed is:

1. A cigarette simulator comprises a cigarette tip, a cylindrical body, fillings, a control valve, and an audio-visual mechanism, said cigarette tip has its one end filled with a filtering material constituting filter, and its other end is connected with one end of the cylindrical body, which includes ventholes at its middle, a cavity between the cigarette tip and the cylindrical body forms flavor medium cylinder filled with the fillings, the cylindrical body has in it the control valve at its end close to the cigarette tip, the control valve is connected with inner cylindrical body, inside the inner cylindrical body is an electrically conducting front inner plate having a hollow hole, the inner cylindrical body is in a shape of an upset trumpet at its end close to the cigarette tip, over which there is an upper cover, two magnetic rings are set at the bottom of the upper cover and at a root of the trumpet of the inner cylindrical body, the two magnetic rings have opposite magnetic poles, a middle portion of the upper cover is fixed with one end of "T" shaped or "τ" shaped conducting wire going through a central hole of the inner plate, an end of the cylindrical body opposite the cigarette tip has at its inner side a fork-shaped splint, a power source, and a lamp socket; on the splint is fixed an integrated circuit module controlling the audio-visual mechanism, on outer wall of the cylindrical body are ventholes, power source is a button battery connected with a conducting wire to the audio-visual mechanism, the lamp socket is cylindrical, in the middle of which are two small holes used as fixing holes for two poles of light-emitting part, end portion of the cylindrical body is connected with cap cover.

2. The cigarette simulator as claimed in claim 1, wherein the fillings in the flavor medium cylinder comprise a volatile cigarette perfume extract and one of the prescription A, B, C, D, or E by weight parts:

A. dichroa leaf 15–20, sesame leaf 25–35, licorice 6–10, borneol 10–15, mugwort leaf 18–23 and mint 15–20;

B. asarum 10–15, mint 10–15, perilla leaf 15–18, nardostachys 10–15, cinnamon 6–10, angelica 25–35, borneol 10–15, and chrysanthemum 18–23;

C. tussilago 15–20, cynachum 10–15, acorus 5–20, perilla leaf 25–35 and sesame leaf 25–35;

D. borneol 10–15, sandalwood 25–35, acorus 15–20, asarum 12–18 and licorice 6–10;

E. ganoderma 15–20, cinnamon 10–15, asarum 12–18, bearded scutellaria 19–23, oldenlandia 25–35 and pepper 10–15;

wherein the ratio of the weight parts for the various components of the volatile cigarette perfume extract is: osmanthus leaf oil 19–23, flavor lemonade oil 15–20, isobutyl salicylate 10–15, phenylethanol 10–15 and anisaldehyde 10–1.

3. The cigarette simulator as claimed in claim 1, wherein the cap cover is a transparent material.

* * * * *

UNITED STATES PATENT AND TRADEMARK OFFICE
CERTIFICATE OF CORRECTION

PATENT NO.     : 6,854,470 B1
DATED          : February 15, 2005
INVENTOR(S)    : D. Pu It is certified that error appears in the above-identified patent and that said Letters Patent is hereby corrected as shown below:

<u>Title page,</u>
Item [30], Foreign Application Priority Data, "97107802 A" should read
-- 97107802.5 --

Signed and Sealed this

Twenty-sixth Day of July, 2005

JON W. DUDAS
*Director of the United States Patent and Trademark Office*

UNITED STATES PATENT AND TRADEMARK OFFICE
CERTIFICATE OF CORRECTION

PATENT NO. : 6,854,470 B1
DATED : February 15, 2005
INVENTOR(S) : D. Pu

It is certified that error appears in the above-identified patent and that said Letters Patent is hereby corrected as shown below:

<u>Title page,</u>
Item [30], Foreign Application Priority Data, "Jan. 12, 1997" should read -- Dec. 1, 1997 --.

Signed and Sealed this

Twenty-seventh Day of December, 2005

JON W. DUDAS
*Director of the United States Patent and Trademark Office*